(12) United States Patent
Piacenza

(10) Patent No.: US 6,207,201 B1
(45) Date of Patent: *Mar. 27, 2001

(54) SODIUM HYPOCHLORITE BASED DISINFECTANT AND STERILIZER FOR MEDICAL-SURGICAL INSTRUMENTS

(75) Inventor: Giuseppe Piacenza, Genoa (IT)

(73) Assignee: Amuchina International, Inc., Gaithersburg, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/765,047

(22) PCT Filed: Jun. 3, 1993

(86) PCT No.: PCT/US93/05091

§ 371 Date: May 23, 1997

§ 102(e) Date: May 23, 1997

(87) PCT Pub. No.: WO94/28722

PCT Pub. Date: Dec. 22, 1994

(51) Int. Cl.[7] .......................... A01N 59/00; A01N 59/08; A61L 2/18; C25B 1/26
(52) U.S. Cl. .................. 424/665; 424/661; 424/663; 422/29; 422/37; 205/500; 510/370; 510/380; 252/187.24; 252/187.25; 252/187.26
(58) Field of Search .................. 422/37, 29; 424/661, 424/665, 663; 252/187.26, 187.24, 187.25; 205/500; 510/370, 380

(56) References Cited

U.S. PATENT DOCUMENTS

| Re. 29,473 | * 11/1977 | Fitzgerald, Jr. | 510/370 |
|---|---|---|---|
| 4,167,561 | 9/1979 | Lamberti | 424/665 |
| 4,390,448 | 6/1983 | Boden | 252/187.26 |
| 4,560,455 | * 12/1985 | Porta et al. | 205/701 |
| 4,786,380 | * 11/1988 | van Duin et al. | 210/748 |
| 4,898,681 | 2/1990 | Burton | 424/665 |
| 4,983,161 | * 1/1991 | Dadson et al. | 604/28 |
| 5,622,848 | * 4/1997 | Morrow | 435/173.1 |
| 5,674,537 | * 10/1997 | Morrow | 424/613 |
| 5,902,619 | * 5/1999 | Rubow et al. | 426/235 |

FOREIGN PATENT DOCUMENTS

| 0 030 401 | 7/1981 | (EP) . |
|---|---|---|
| 2 572 419 | 5/1986 | (FR) . |
| 2021947 | 12/1979 | (GB) . |

OTHER PUBLICATIONS

Parkes, G. D., Mellor's Modern Inorganaic Chemistry, Longmans, Green and Co., NY, pp. 512–513, 1951.*
Chemical Abstracts 132: 83331b (2000).*
Chemical Abstracts 129: 46719b (1998).*
Chemical Abstracts 128: 274847b (1998).*
Chemical Abstracts 127: 350949h (1997).*
Chemical Abstracts 125: 338594q (1996).*
Chemical Abstracts 100: 173413y (1984).*

* cited by examiner

Primary Examiner—John Pak
(74) Attorney, Agent, or Firm—Finnegan, Henderson, Farabow, Garrett & Dunner, L.L.P.

(57) ABSTRACT

A first embodiment of the present invention is directed to an aqueous disinfectant solution comprising an alkali metal or alkaline earth metal hypochlorite, an amount of base sufficient to raise the pH of the solution to at least 12, and water. A second embodiment of the present invention is directed to a method for sterilizing medical and dental instruments and hard surfaces which comprises contacting the medical or dental instruments or hard surfaces with an aqueous disinfecting solution comprising an alkali metal or alkaline earth metal hypochlorite, an amount of a base sufficient to raise the pH of the solution to at least 12, and water, for a time sufficient to disinfect the medical or dental instruments or hard surface.

16 Claims, No Drawings

SODIUM HYPOCHLORITE BASED DISINFECTANT AND STERILIZER FOR MEDICAL-SURGICAL INSTRUMENTS

This application is a 371 of PCT/US93/05091, filed on Jun. 3, 1993.

FIELD OF THE INVENTION

The present invention relates to a composition containing an alkali metal or alkaline earth metal hypochlorite as the active ingredient for the disinfection and sterilization of hard surfaces and plastic, metal and glass instruments for surgery and dentistry. The present invention also relates to a method of disinfecting or sterilizing hard surfaces or surgical and dental instruments with solutions of alkali metal or alkaline earth metal hypochlorites.

BACKGROUND OF INVENTION

Since the 18th century, chlorine-based disinfectants have been employed in medical applications for their rapid, potent and broad-spectrum bactericidal activity. For example, Dakin developed a chlorine solution which subsequently proved useful for lavaging foul wounds. See H. D. Dakin, *Brit. Med. J.*, ii:809 (December 1915). Chlorine Has also been widely used as a germicide in water and sewage Treatment.

Among the useful chlorine-based disinfectants are alkali metal and alkaline earth metal hypochlorites. Sodium, potassium, lithium and calcium hypochlorites are known for their disinfecting and bleaching properties. See e.g., U.S. Pat. No. 3,717,580 to Echols et al.

Despite the long history of efficacious use of chlorine-based disinfectants, few chlorine compounds are used today as sterilants in medical and dental practice. The many problems associated with chlorine-based disinfectants limit their usefulness for disinfecting or sterilizing instruments or hard surfaces. For example, the instability of the active ingredient causes the effectiveness of some hypochlorite disinfectant solutions to deteriorate significantly within a few hours of preparation.

An even more significant problem associated with use of chlorine-based disinfectants, however, is the highly corrosive nature of these solutions due to high oxidation potential. For example, concentrations of hypochlorous acid sufficient to sterilize standard bacteriological challenges also quickly attack metals, even stainless steel, causing discoloration and pitting. Metal instruments soaked in chlorine solutions tend to be irreversibly damaged; sharp edges are destroyed and metal surfaces are pitted and darkened.

As a result, corrosion inhibitors have been recommended for use with hypochlorites. See, e.g., G. H. Botham et al., "Corrosion by Commercial Sodium Hypochlorite and its Inhibition," *J. Dairy Res*, vol. 16, 37 (1949). The use of corrosion inhibitors, however, has been plagued with problems, such as the reactivity of many inhibitors with chlorine and the resulting deactivation of the disinfectant solution.

Accordingly, there is a great need in the medical and dental arts for a disinfectant which will allow the rapid and effective sterilization of medical and dental instruments and hard surfaces at room temperature without corrosive effects and which exhibits sufficient chemical stability.

SUMMARY OF INVENTION

A first embodiment of the present invention is directed to an aqueous disinfectant solution comprising an alkali metal or alkaline earth metal hypochlorite, an amount of base sufficient to raise the pH of the solution to at least 12, and water.

A second embodiment of the present invention is directed to a method for sterilizing medical and dental instruments and hard surfaces which comprises contacting the medical or dental instruments or hard surface with an aqueous disinfecting solution comprising an alkali metal or alkaline earth metal hypochlorite, an amount of a base sufficient to raise the pH of the solution to at least 12, and water, for a time sufficient to disinfect the medical or dental instruments or hard surface.

DESCRIPTION OF PREFERRED EMBODIMENTS

The present invention is directed to an aqueous disinfectant solution which comprises an alkali metal or alkaline earth metal hypochlorite, an amount of base sufficient to raise the pH of the solution to at least 12, and water. The disinfectant solution according to the present invention allows for the rapid and effective sterilization of medical and dental instruments and hard surfaces, without corrosion of metal or damage to plastic, optical fibers or glass.

The active ingredient in the aqueous disinfectant solution is an alkali metal or alkaline earth metal hypochlorite. Preferably, the active ingredient is an alkali metal hypochlorite. More preferably, the alkali metal hypochlorite is sodium hypochlorite.

Sodium hypochlorite is commercially available from sources such as Sigma®. A particularly preferred sodium hypochlorite is commercially available from Amuchina, Inc. under the name AMUCHINA®. AMUCHINA® sodium hypochlorite is an electrolytic chloroxidizer which provides 11 grams of chlorine per liter. The use of AMUCHINA® electrolyte chloroxidizer in the present invention is particularly preferred on account of the high purity with respect to metal content and increased stability of the active agent in AMUCHINA® electrolytic chloroxidizer as compared to other commercially available sodium hypochlorites.

The amount of alkali metal or alkaline earth metal hypochlorite employed in the aqueous disinfectant solution according to the present invention can be the minimum amount needed to show a positive disinfecting effect in any of the known methods for determining disinfecting capacity, such as standard bacteriological challenges, or such higher concentrations as may be appropriate. In general, any amount which elicits disinfecting effects is appropriate. The amount of hypochlorite employed is preferably sufficient to provide a concentration of available chlorine within the range of 225.0 to 287.5 parts per million. When sodium hypochlorite is employed in the aqueous disinfectant solution, 0.0225 to 0.0288 grams of sodium hypochlorite (as available chlorine) are preferably used per 100 milliliters of solution.

According to the present invention, the aqueous disinfectant solution also contains a base. The base may be any of the known compounds which cause an aqueous solution to have an alkaline pH, i.e., a pH greater than 7. Suitable bases are readily available from commercial sources, such as Sigma®. Preferably, the base employed in the aqueous disinfectant solution is an alkali metal or alkaline earth metal base. Particularly preferred are the alkali metal and alkaline earth metal hydroxides. Most preferred is sodium hydroxide.

The amount of base employed in the aqueous disinfectant solution is at least the minimum amount of base sufficient to raise the pH of the solution to at least 12. Preferably, the amount of base employed is sufficient to raise the pH of the aqueous disinfectant solution to within the range of 12 to 13. When sodium hydroxide is employed as the base, 3.6 to 4.4 grams of sodium hydroxide are preferably used per 100 milliliters of solution.

A preferred embodiment of the present invention comprises: 0.0225 to 0.0288 grams of sodium hypochlorite (as available chlorine), 3.6 to 4.4 grams of sodium hydroxide, and purified water sufficient to make 100 milliliters. A particularly preferred embodiment comprises: 0.025 grams of sodium hypochlorite (as available chlorine), 4.0 grams of sodium hydroxide, and purified water sufficient to make 100 milliliters.

In addition to the alkali metal or alkali earth metal hypochlorite and the base, the aqueous disinfectant solution may also contain conventional pharmaceutical additives and excipients. Preferably, the aqueous disinfectant solution also contains sodium chloride. One skilled in the art is able to determine the amount of any additives or excipients based on the intended use. For example, 100 milliliters of the aqueous disinfectant solution according to the present invention preferably also contains 0.35 to 0.45 grams of sodium chloride.

A preferred embodiment of the present invention comprises: 0.0225 to 0.0288 grams of sodium hypochlorite (as available chlorine), 3.6 to 4.4 grams of sodium hydroxide, 0.35 to 0.45 grains of sodium chloride, and purified water sufficient to make 100 milliliters. A particularly preferred embodiment comprises: 0.025 grams of sodium hypochlorite (as available chlorine), 4.0 grams of sodium hydroxide, 0.39 grams of sodium chloride, and purified water sufficient to make 100 milliliters.

The aqueous disinfectant solution according to the present invention may be prepared by any of the methods known to those skilled in the art. Preferably, the alkali metal or alkaline earth metal hypochlorite, the base, and water are added to a mixer and mixed at low speed for a time sufficient to prepare the aqueous disinfectant solution. During mixing, the solution can be sampled and tested for available chlorine, pH, and concentration of base. Preferably, the amount of available chlorine is within the range of 225.0 to 287.5 parts per million and the pH is within the range of 12 to 13. When sodium hydroxide is used as the base, the concentration of sodium hydroxide is preferably within the range of 3.6 to 4.4%.

The aqueous disinfectant solution according to the present invention may be used to sterilize and disinfect rapidly and effectively medical and dental instruments and hard surfaces. The aqueous disinfectant solution may be used to disinfect and sterilize metal surgical instruments, such as scalpels, plastic instruments, such as face masks, catheters, couplings, pipes for connections, collectors, and tubes for respiration, instruments with lenses, such as endoscopes, and instruments and devices used in dentistry. The aqueous disinfectant solution may also be used to disinfect hard surfaces, such as tables and floors.

The aqueous disinfectant solution according to this invention may be used as a concentrate or diluted 1:5 or 1:10 with water. It is within the skill of the worker in the art to determine the appropriate concentration of the aqueous disinfectant solution based upon the intended application and the desired result.

For the disinfection and sterilization of medical and dental instruments, it is preferred that the aqueous disinfectant solution according to the present invention be poured into a suitable receptacle, such as a basin, and the instruments to be sterilized and disinfected be soaked in the solution for a time sufficient to disinfect and sterilize the instruments. Preferably, the instruments are soaked in the aqueous disinfectant solution for about 15 minutes at room temperature and then washed with sterile physiological solution or sterile distilled water prior to use.

The following examples are merely illustrative of the invention and should not be construed as limiting. One skilled in the art can make, without undue experimentation, various substitutions and variations and by equivalent means, performing in substantially the same manner, obtain substantially the same results without departing from the teaching and spirit of the invention.

EXAMPLES

Example 1

The following ingredients were poured into a 10 l mixer:

| | |
|---|---|
| purified water F.U. IX | 8.4393 l |
| AMUCHINA ® electrolytic chloroxidizer (11 g/l available chlorine) | 0.2273 l |
| sodium hydroxide 30% | 1.3334 l |

The mixer was turned on at low speed for 1 hour. Samples were taken at intervals to test for available chlorine (225.0–287.5 ppm), pH (12.0–13.0), sodium chloride (0.35–0.45%) and sodium hydroxide (3.6–4.4%).

Example 2

The following ingredients were poured into a 10 l mixer:

| | |
|---|---|
| purified water F.U. IX | 8.6520 l |
| sodium hypochlorite 18% (17.1% available chlorine) | 0.0146 l |
| sodium hydroxide 30% | 1.3334 l |

The mixer was turned on at low speed for 1 hour. Samples were taken at intervals to test for available chlorine (225.0–287.5 ppm), ph (12.0–13.0), and sodium hydroxide (3.6–4.4%).

Although preferred embodiments of the invention are described herein in detail, it will be understood by those skilled in the art that variations may be made thereto without departing from the spirit of the invention or the scope of the appended claims.

What is claimed is:

1. An aqueous disinfectant composition consisting essentially of:
   (A) an electrolyzed chloroxider solution which:
      (i) contains sodium hypochlorite, and
      (ii) provides 11 g of available chlorine per liter of said solution:
   (B) an amount of alkali metal or alkaline earth metal base sufficient to raise the pH of said composition to at least 12;
   (C) sodium chloride; and
   (D) water.

2. The aqueous disinfectant composition according to claim 1, wherein said base is an alkali metal hydroxide.

3. The aqueous disinfectant composition according to claim 2, wherein said alkali metal hydroxide is sodium hydroxide.

4. The aqueous disinfectant composition according to claim 1, wherein the pH of said composition is within the range of 12 to 13.

5. The aqueous disinfectant composition according to claim 1, wherein 100 milliliters of said aqueous disinfectant composition consists essentially of: a dilute electrolyzed chloroxidizer solution having 0.0225 to 0.0288 g of available chlorine, 3.6 to 4.4 g sodium hydroxide, sodium chloride and water sufficient to make 100 milliliters.

6. The aqueous disinfectant composition according to claim 5, wherein a dilute electrolyzed chloroxidizer solution having 0.025 g of available chlorine, 4.0 g sodium hydroxide, sodium chloride and water sufficient to make 100 milliliters are present.

7. A method of disinfecting medical and dental instruments and hard surfaces which comprises contacting the medical or dental instruments or hard surfaces with an effective amount of an aqueous disinfectant composition consisting essentially of:
   (A) an electrolyzed chloridizer solution which:
      (i) contains sodium hypochlorite, and
      (ii) provides 11 g of available chlorine per liter of said solution;
   (B) an amount of alkali metal or alkaline earth metal base sufficient to raise the pH of said composition to at least 12;
   (C) sodium chloride; and
   (D) water.

8. The method according to claim 7, wherein said medical or dental instrument or hard surface is contacted with said aqueous disinfectant composition for 15 minutes.

9. The method according to claim 7, wherein said base is an alkali metal hydroxide.

10. The method according to claim 9, wherein said alkali metal hydroxide is sodium hydroxide.

11. The method according to claim 7, wherein the pH of said composition is within the range of 12 to 13.

12. The method according to claim 7, wherein 100 milliliters of said aqueous disinfectant composition consists essentially of a dilute electrolyzed chloroxidizer solution having 0.0225 to 0.0288 g of available chlorine, 3.6 to 4.4 g sodium hydroxide, sodium chloride and water sufficient to make 100 milliliters.

13. The method according to claim 12, wherein 100 milliliters of said aqueous disinfectant composition consists essentially of a dilute electrolyzed chloroxidizer solution having 0.025 g of available chlorine, 4.0 g sodium hydroxide, sodium chloride and water sufficient to make 100 milliliters.

14. An aqueous disinfectant composition consisting essentially of a diluted electrolyzed chloroxidizeer solution which contains sodium hypochlorite and provides 11 g of available chlorine per liter of solution, an amount of alkali metal or alkaline earth metal base sufficient to raise the pH of said composition to at least 12, sodium chloride, and water.

15. The aqueous disinfectant composition according to claim 14, wherein 100 milliliters of said aqueous disinfectant composition consists essentially of a dilute electrolyzed chlorixidizer solution having 0.0225 to 0.0228 g of available chlorine, 3.6 to 4.4 g sodium hydroxide, 0.35 to 0.45 g sodium chloride, and water sufficient to make 100 milliliters.

16. The aqueous disinfectant composition according to claim 15, wherein for 100 milliliters: a dilute electrolyzed chlorixidizer solution having 0.0225 g of available chlorine, 4.0 g sodium hydroxide, 0.39 g sodium chloride and water sufficient to make 100 milliliters are present.

* * * * *

UNITED STATES PATENT AND TRADEMARK OFFICE
CERTIFICATE OF CORRECTION

PATENT NO. : 6,207,201 B1
DATED : March 27, 2001
INVENTOR(S) : Giuseppe Piacenza It is certified that error appears in the above-identified patent and that said Letters Patent is hereby corrected as shown below:

<u>Title page,</u>
Item [57], in the Abstract, line 8, " hard surfaces" should read -- hard surface --.

<u>Column 4, claim 1,</u>
Line 53, "chloroxider" should read -- chloroxidizer --.
Line 56, "solution:" should read -- solution; --.

<u>Column 5, claim 7,</u>
Line 20, "chloridizer" should read -- chloroxidizer --.

<u>Column 6, claim 14,</u>
Line 17, "chloroxidizeer" should read -- chloroxidizer --.

<u>Column 6, claim 15,</u>
Line 26, "chlorixidizer" should read -- chloroxidizer --.

<u>Column 6, claim 16,</u>
Line 32, "chlorixidizer" should read -- chloroxidizer --; and
"0.0225 g" should read -- 0.025 g --.

Signed and Sealed this

Sixteenth Day of October, 2001

*Attest:*

*Attesting Officer*

NICHOLAS P. GODICI
*Acting Director of the United States Patent and Trademark Office*